(12) United States Patent  
Francese et al.

(10) Patent No.: US 7,473,220 B2  
(45) Date of Patent: Jan. 6, 2009

(54) SURGICAL PORT DEVICE

(75) Inventors: Jose Luis Francese, Miami Springs, FL (US); Matthew A. Palmer, Miami, FL (US); Ralph de la Torre, Swampscott, MA (US)

(73) Assignee: Medcanica, Inc., Miami, FL (US)

( * ) Notice: Subject to any disclaimer, the term of this patent is extended or adjusted under 35 U.S.C. 154(b) by 663 days.

(21) Appl. No.: 10/634,049

(22) Filed: Aug. 4, 2003

(65) Prior Publication Data

US 2005/0049624 A1 Mar. 3, 2005

(51) Int. Cl.
*A61B 1/00* (2006.01)
(52) U.S. Cl. ..................................... 600/184
(58) Field of Classification Search ................. 606/108, 606/213, 1, 185, 167; 604/26, 174, 103.3, 604/332, 175
See application file for complete search history.

(56) References Cited

U.S. PATENT DOCUMENTS

| | | | | | |
|---|---|---|---|---|---|
| 2,064,435 | A | * | 12/1936 | Loeffler | 379/433.01 |
| 2,320,993 | A | * | 6/1943 | Worner | 228/155 |
| 3,717,151 | A | * | 2/1973 | Collett | 604/106 |
| 3,983,879 | A | * | 10/1976 | Todd | 604/96.01 |
| 5,330,497 | A | * | 7/1994 | Freitas et al. | 606/185 |
| 5,423,796 | A | * | 6/1995 | Shikhman et al. | 606/1 |
| 5,817,062 | A | | 10/1998 | Flom et al. | 604/174 |
| 5,830,191 | A | * | 11/1998 | Hildwein et al. | 604/175 |
| 6,228,063 | B1 | * | 5/2001 | Aboul-Hosn | 604/174 |
| 6,432,085 | B1 | | 8/2002 | Stellon et al. | 604/164.04 |
| 6,464,691 | B1 | | 10/2002 | Castaneda et al. | 606/1 |
| 6,537,299 | B1 | * | 3/2003 | Hogendijk et al. | 606/213 |
| 6,814,713 | B2 | * | 11/2004 | Aboul-Hosn et al. | 604/26 |

* cited by examiner

*Primary Examiner*—Todd E Manahan
*Assistant Examiner*—Tuan V Nguyen
(74) *Attorney, Agent, or Firm*—Gordon & Jacobson, PC

(57) ABSTRACT

An improved surgical port device includes a port body with a tubular section having a distal end. A flexible flange is disposed at the distal end. A retention member is slidably mated along the tubular section such that a distance between the retention member and the flexible flange can be adjusted. In this manner, the position of the retention member with respect to the flexible flange is adjustably fixed to clamp portions of a body wall disposed therebetween, thus effectively clamping the port body in place. The flexible flange has an adaptable diameter that is reduced when the port body passes through a narrow opening in the body wall. Preferably, the flexible flange has a conically-shape that butts up against the inner surface of the body wall during use to thereby provide a seal between the body wall and the frusto-conical flange. It may also have an annular projection that projects radially outward from the conical surface of the flange to provide a drip edge that directs fluids around its periphery and thus prevent fluids from flowing over the projection. This reduces the smearing of optical imaging devices that are disposed in the vicinity of the distal end of the device. The surgical port device of the present invention may also be operated to provide improved fields of view for such optical imaging devices.

15 Claims, 7 Drawing Sheets

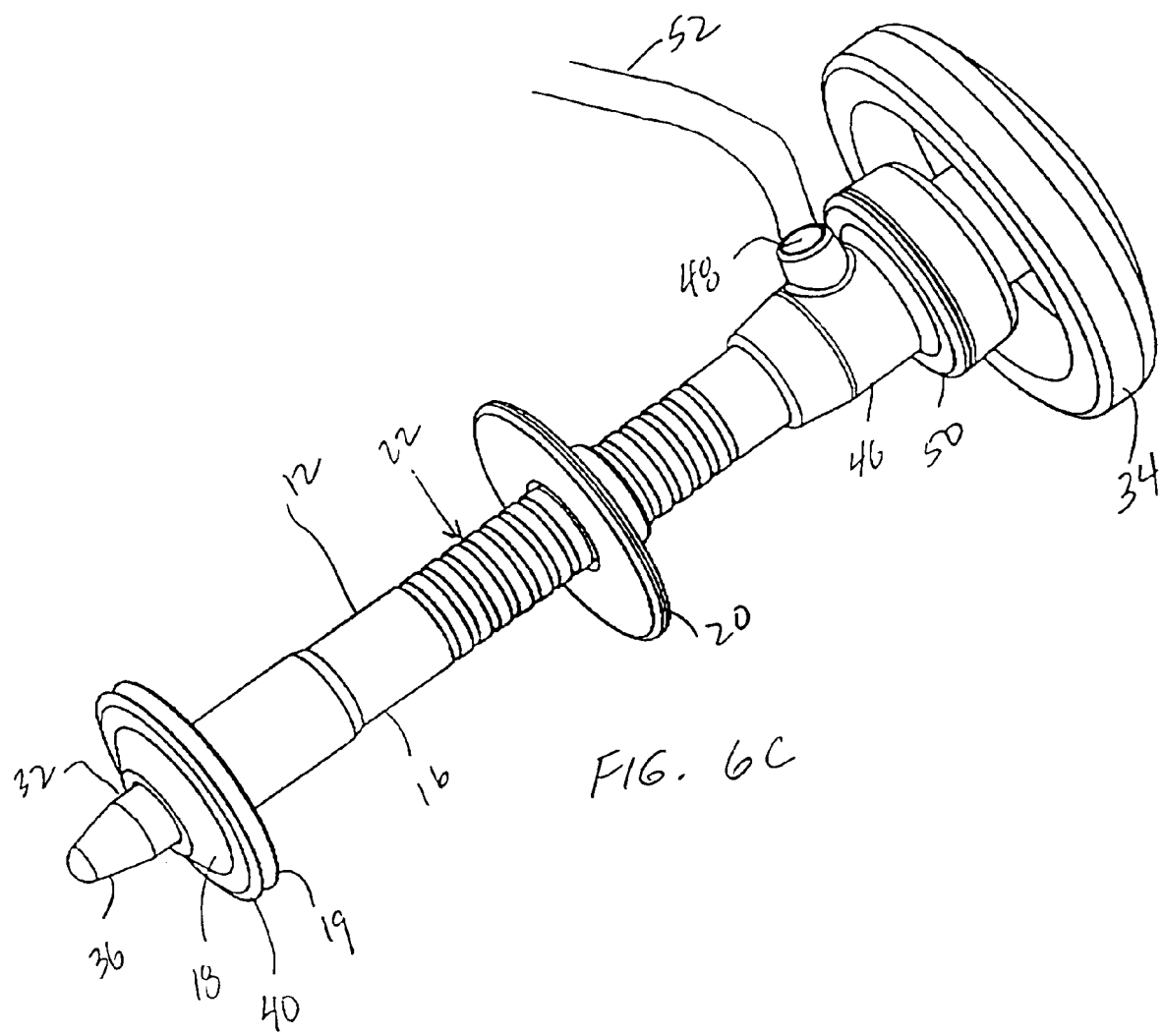

SURGICAL PORT DEVICE

BACKGROUND OF THE INVENTION

1. Field of the Invention

This invention relates broadly to surgical instruments. More particularly, this invention relates to ports for surgical instruments. In addition, the invention relates to an improved technique for performing surgery through a surgical port device.

2. State of the Art

Endoscopic surgical procedures are facilitated by the use of surgical ports (commonly referred to as "trocars") that provide access into the human body. Various endoscopic surgical instruments (e.g., imaging probes, cutting blades, clamps/suturing devices, etc.) are inserted into a body cavity (such as the chest cavity) via such ports and are manipulated in the cavity. Surgical ports are also used in laparoscopic surgical procedures to provide access into the abdominal cavity for insertion and manipulation of various laparoscopic surgical instruments therein. Typically, such surgical ports employ a cannula as the passageway for the various endoscopic/laparoscopic instruments. Often, internal pressures in the body cavity are elevated by insufflation via an external pressure source operably coupled to the body cavity through an inlet in the surgical port. In such configurations, the surgical ports often employ gaskets disposed upstream from the inlet that maintain the elevated internal pressures in the body cavity while inserting/removing instruments through the cannula of the port.

U.S. Pat. No. 5,817,062 to Flom et al. and U.S. Pat. No. 5,830,191 to Hildwein et al. disclose two exemplary surgical ports. Each employs a flexible member at the distal end of a tubular structure in addition to a flange fixed in place at the proximal end of the tubular structure. However, the surgical ports of U.S. Pat. Nos. 5,817,062 and 6,830,191 suffer from many drawbacks, and are not widely used commercially.

A first drawback to these ports in the fixed distance between the flexible member and the flange of the respective surgical ports. Thus, these surgical ports employ a clamping action of body tissue between the flexible member and the flange for a limited range of body wall thicknesses, and are effective in securely affixing the surgical port to the entrance site over this limited range of body wall thickness. In the event that the body wall of the entrance site lies outside this limited range (e.g., the body wall is too small or too big), the effectiveness of such surgical ports is adversely impacted.

A second drawback arises when body secretions and blood runs down the inside surface of the body cavity and flows over the flexible member. This fluid can interfere with proper operation of the medical instrument inserted through the surgical port. For example, it is commonplace for the optics of an endoscope/laparoscope to be retracted such that the optics are positioned essentially flush to the inside surface of the body wall. This configuration maximizes the field of view of the optics within the body cavity. However, in this configuration, any body fluid that flows down the inside surface of the body cavity in the vicinity of the surgical port will smudge the optics. The operator is then required to remove the endoscope/laparoscope from the surgical port, clean the fluid from the optics, and reinsert the endoscope/laparoscope through the surgical port. This extended procedure causes safety concerns and physician frustration, and extends the procedure time.

The surgical port of U.S. Pat. No. 5,830,191 also suffers from the drawback that its tubular structure is flexible and thus fails to provide structural support for non-rigid instruments that pass through it. When the orientation of the port is manipulated such that its angle of entry diverges substantially from the angle of the entrance site made through the body wall, the body wall exerts forces on the flexible tubular structure such that its binds on the surgical instrument passing therethrough. This binding action interferes with normal operation of the surgical instrument (i.e., the surgical instrument is not able to freely move through the port).

Thus, there remains a need in the art for improved surgical port devices that overcome the limitations provided by these prior art port devices.

SUMMARY OF THE INVENTION

It is therefore an object of the invention to provide a surgical port device having an adjustable distance between the body tissue clamping elements such that it is effective over a wide range of body wall thicknesses, and thus is effective in securely affixing the surgical port device to the entrance site over a wide range of body wall thickness.

It is another object of the invention to provide a surgical port device that limits the body secretions and blood that run down the inside surface of the body cavity and flow over the internal clamping member of the surgical port device, which potentially causes interference with the proper operation of instruments disposed in the vicinity of the internal clamping member.

It is a further object of the invention to provide a surgical port device that can be quickly and easily inserted through and affixed to the body wall.

It is also an object of the invention to provide a surgical port device that is inexpensive to manufacture.

It is an additional object of the invention to provide a surgical port device that can be manipulated to afford improved field of views of optical imaging devices (e.g., endoscopes) used in conjunction therewith.

It is still another object of the invention to provide a surgical port device that affords structural support for non-rigid instruments.

It is yet another object of the invention to provide a surgical port device that enables the orientation of the surgical port device to be manipulated such that its angle with respect to the body cavity can vary without interfering with user manipulation of instruments used in conjunction therewith (for example, enabling an endoscope to freely move through the surgical port device while the orientation of the surgical port device is varied).

In accord with these objects, which will be discussed in detail below, an improved surgical port device includes a port body with a tubular section having a distal end. A flexible flange is disposed at the distal end. A retention member is slidably mated along the tubular section such that a distance between the retention member and the flexible flange can be adjusted. In this manner, the position of the retention member relative to the flexible flange is adjustably fixed to clamp portions of a body wall disposed therebetween, thus effectively clamping the port body in place. The flexible flange has an adaptable cross-sectional diameter that is reduced when the port body passes through a narrow opening in the body wall.

According to one embodiment of the invention, the flexible flange has a frusto-conical shape that butts up against the inner surface of the body wall during use to thereby provide a seal between the body wall and the frusto-conical flange. It may also have an annular projection that projects radially outward from the conical surface of the flange to provide a drip edge that directs fluids around its periphery and thus prevent fluids from flowing over the projection. This reduces the smearing of optical imaging devices that are disposed in the vicinity of the distal end of the device.

According to another aspect of the present invention, the improved surgical port device may be partially retracted to provide improved fields of view for optical imaging devices used in conjunction therewith.

Additional objects and advantages of the invention will become apparent to those skilled in the art upon reference to the detailed description taken in conjunction with the provided figures.

BRIEF DESCRIPTION OF THE DRAWINGS

FIGS. 6A, 6B and 6C are perspective views illustrating an alternate embodiment of a surgical port device in accordance with the present invention.

DETAILED DESCRIPTION OF THE PREFERRED EMBODIMENTS

As used herein, the term "distal" is generally defined as in the direction of the patient and pertinent body cavity, or away from a user of the device. Conversely, "proximal" generally means in the direction away from the patient/pertinent body cavity, or toward the user of the device.

Figure 1:
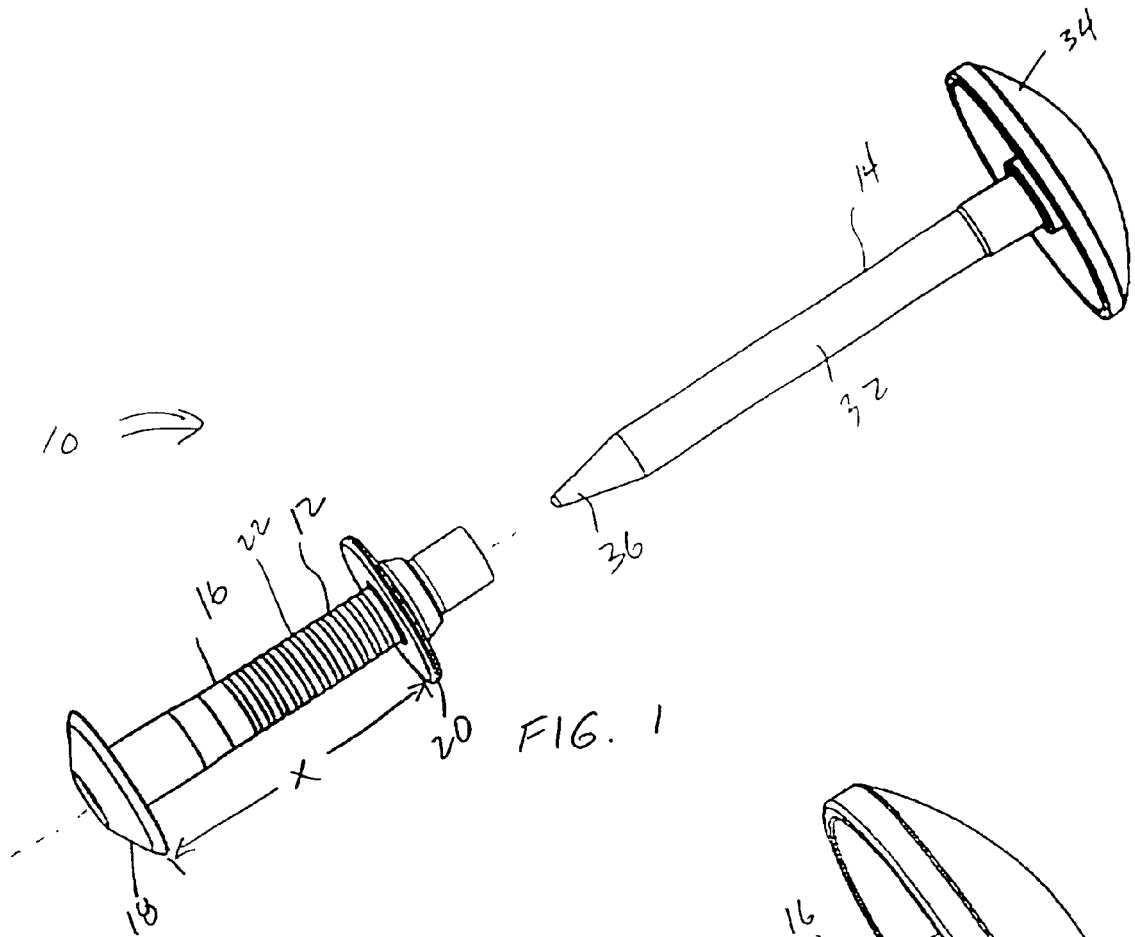
FIG. 1 is a disassembled perspective view of a surgical port device according to the present invention.
Figure 2:
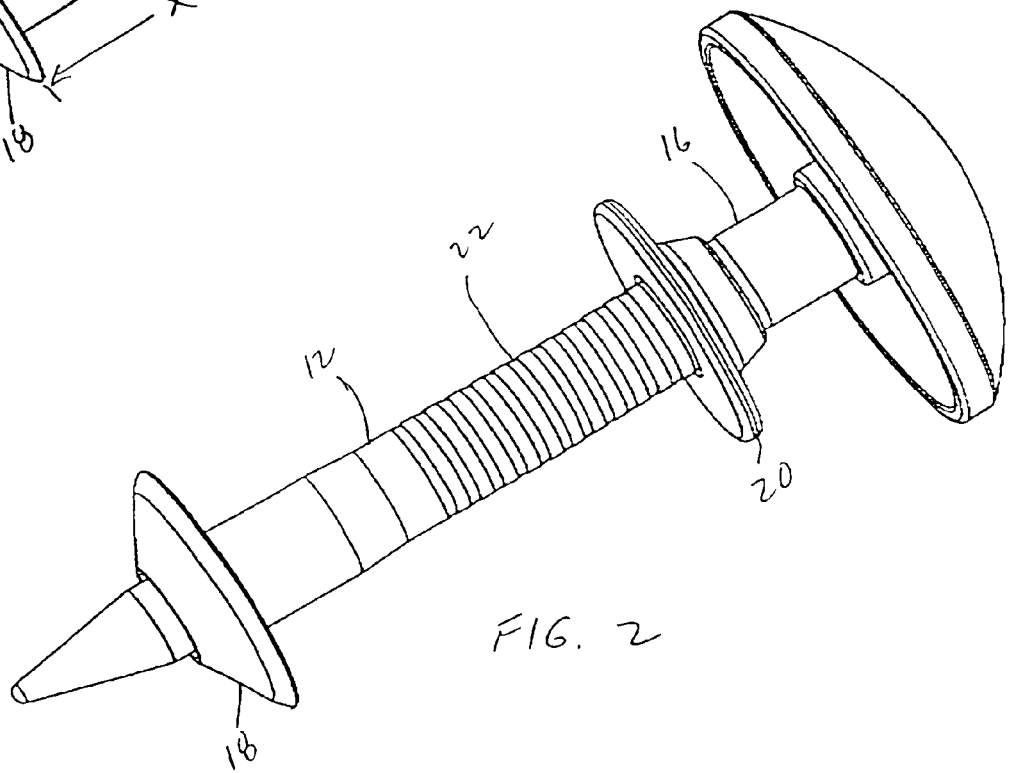
FIG. 2 is a perspective view of the surgical port device of FIG. 1 with the obturator inserted into the port body.
Figure 3:
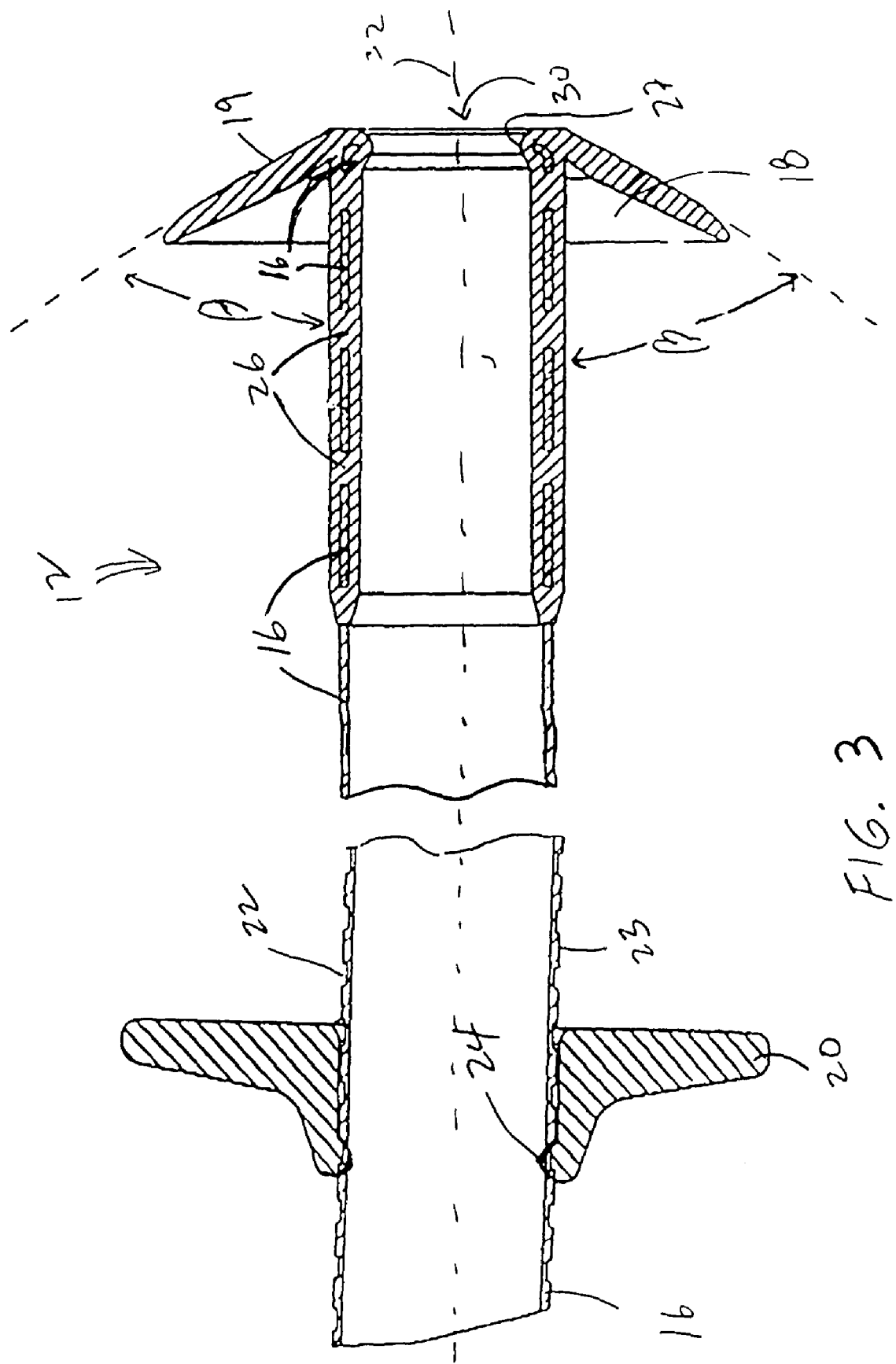
FIG. 3 is a broken cross-sectional view of the port body of FIGS. 1 and 2.

Turning now to FIGS. 1 and 2, there is shown an improved surgical port device in accordance with the present invention, including a port body 12 and an obturator 14. The port body 12 includes a rigid tubular section 16 having a flexible frusto-conical flange 18 disposed at its distal end. The outer surface 19 of the flange 18 is proximally-concave (e.g., oriented toward the proximal end of the tubular section or cannula 16 at an angle β less than 90°) as best shown in FIG. 3. A retention member 20 is slidably mated along the rigid tubular section 16 such the distance X between the retention member 20 and the flange 18 can be adjusted. As described in detail below, the position of the retention member 20 with respect to the flange 18 is fixably adjusted to clamp portions of the body wall disposed therebetween and thus effectively clamp the port body 12 in place. In the preferred embodiment, adjustment of the position of the retention member 20 along the tubular section 16 is provided by a plurality of annular grooves 22 in the outer surface 23 of the rigid tubular section 16 that cooperate with a flexible ring pall 24 of the retention member 20 as best shown in FIG. 3. The pall 24 slides easily in the distal direction (e.g., from the proximal end of the tubular section 16 toward the distal end of the tubular section 16) over the annular grooves 22; yet, the pall 24 resists sliding in the proximal direction (e.g., from the distal end of the tubular section 16 toward the proximal end of the tubular section 16) by engaging one of the annular grooves 22. In this manner, the position of the retention member 20 can be adjusted such that the retention member 20 and flange 18 effectively clamp the port body 12 in place.

Preferably, the flexible flange 18 is integrally formed at the distal end of tubular section 16 via injection molding of material through one or more windows 26 (FIG. 3) in the tubular section 16. In this manner, the flexible flange 18 is formed in place with the tubular section 16. In addition, the tubular section 16 is preferably rolled over at its distal end such that flexible flange 18 includes an annular projection 27 which projects radially inward and covers the rolled-over distal end of the tubular section 16. Advantageously, these structural features minimizes tearing of the flexible flange 18 as the port device is inserted through and secured to the body wall as described below in detail. Moreover, the flexible flange 18 is preferably formed of a hydrophobic material, or is treated with a coating which promotes "beading" and rolling of fluids.

The tubular section 16 and the flange 18 define a passageway 30 (FIG. 3) through which surgical instruments are inserted and manipulated during surgical operations performed with the port device 12 secured in place to the body wall. The obturator 14 includes a rod (or tube) section 32 having a handle 34 at its proximal end and a conically-tapered tip 36 at its distal end. The rod section 32 and tip 36 of the obturator 14 are capable of being inserted into the passageway 30 of the port body 12 such that the tip 36 extends from the distal end of the flange 18 as shown in FIG. 2.

In order to secure the port device to the body wall of a patient, an incision (typically on the order of 7-8 mm in length) is made into the skin at the desired entry site for the port device. In conjunction with the incision, the body wall (or portions thereof) may be dissected at the desired entry site. The obturator 14 is inserted into the passageway 30 of the port body 12 such that the tip 36 extends from the distal end of the flange 18 as shown in FIG. 2.

Figure 4A:
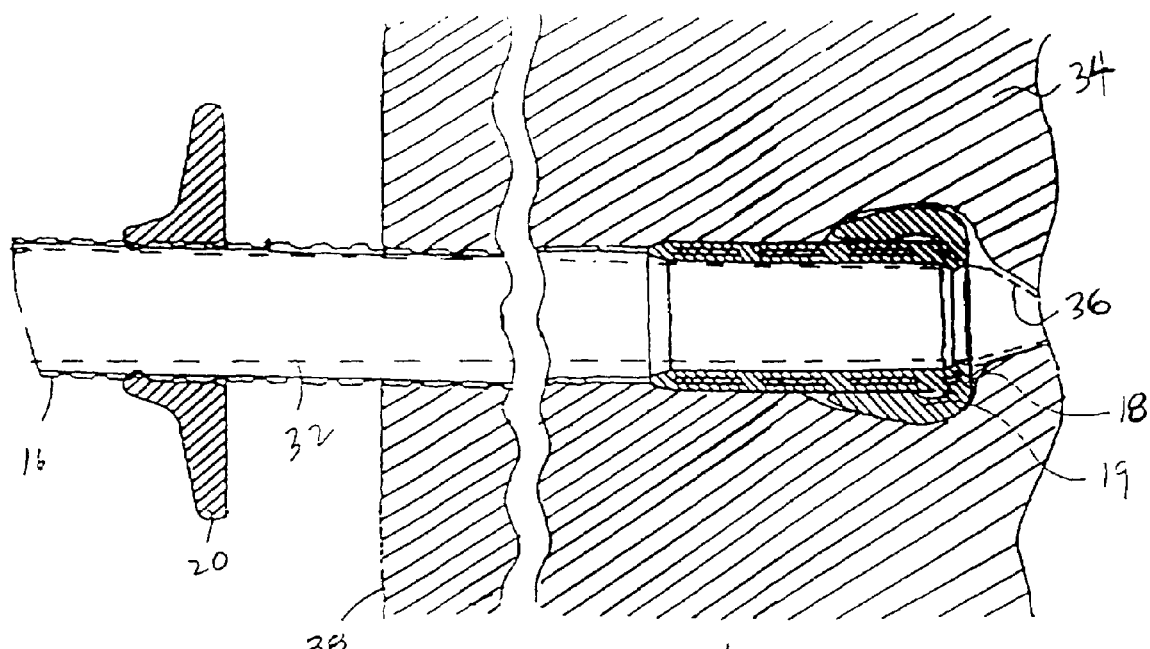
FIG. 4A is a broken cross-sectional view showing the surgical port of FIGS. 1 and 2 being inserted into the body whereby the flange folds back in the proximal direction to provide a reduced cross-sectional diameter that facilitates such insertion.
Figure 4B:
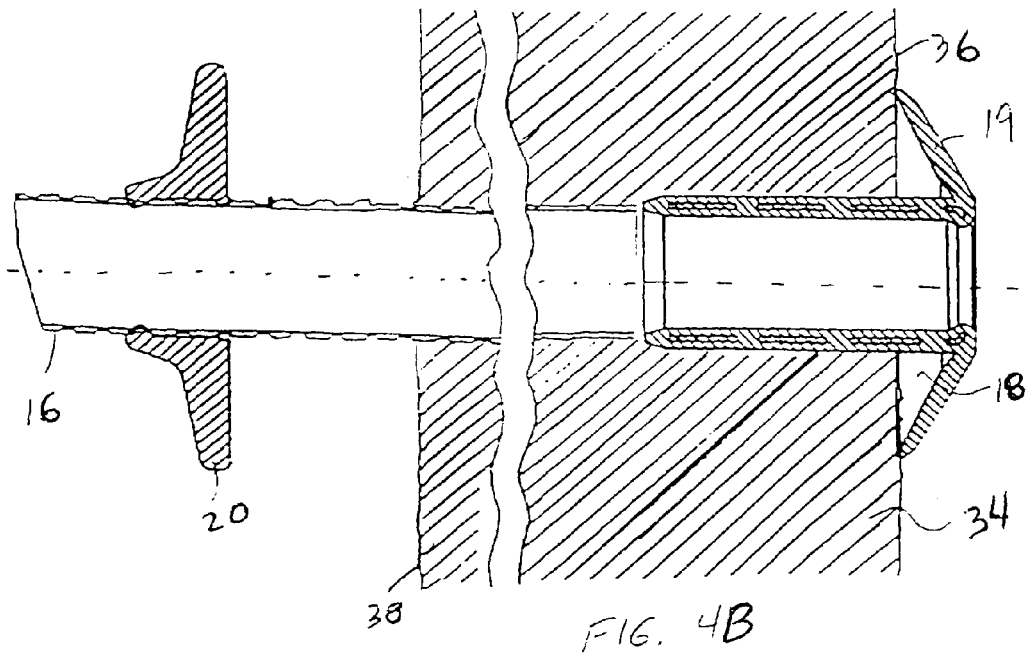
FIG. 4B is a broken cross-sectional view showing the surgical port of FIGS. 1 and 2 after insertion into the body whereby the flange returns back to its original shape.

The obturator 14 and port body 12 (including the flexible flange 18) are then pushed through a narrow opening in the body wall at the entrance site. During this operation as seen in FIG. 4A, the resistive forces exerted by the elastic nature of the body wall causes the outer surface 19 of the flexible flange 18 to fold in the proximal direction (i.e., toward the proximal end of the tubular section 16) and radially inward (i.e., toward the longitudinal axis of the tubular section 16). Once in the body cavity as seen in FIG. 4B, the outer surface 19 of the flange 18 deploys back to its original frusto-conical shape. In this manner, the flexible flange 18 deforms to provide a decreased cross-sectional diameter as it passes through the narrow opening in the body wall at the entrance site, and returns to an increased cross-sectional diameter when it passes through the body wall and enters the body cavity.

Figure 4C:
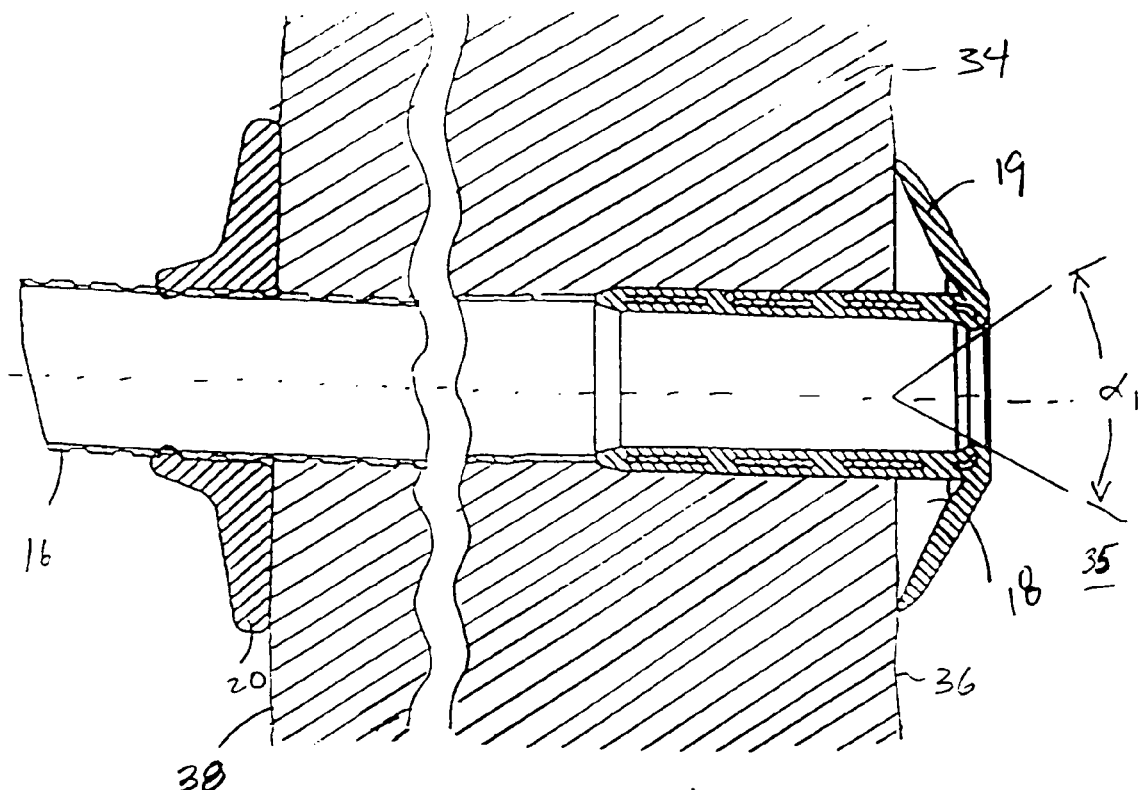
FIG. 4C is a broken cross-sectional view of the port body of FIGS. 1 and 2 whereby the flange and retention member are positioned to effectively clamp a body structure therebetween.

The obturator 14 is removed from the port body 12, and the retention member 20 is moved in the distal direction while pulling the tubular section 16 such that flange 18 butts up against the inside surface 36 of the body wall 34 at the entrance site. During this operation as seen in FIG. 4C, the retention member 20 is moved (ratcheted) in the distal direction until it butts up against the outside surface 38 of the body wall in the vicinity of the entrance site, thereby clamping the port body 12 to the body wall at the entrance site. In the preferred embodiment shown, the ring pall 24 of the retention member 20 ratchets in the proximal direction by engaging one of the annular grooves 22 of the tubular section. In this manner, the position of the retention member 20 is adjusted such that the retention member 20 and flange 18 effectively clamp and secure the port body 12 in place as shown in FIG. 4C. In addition, because the flange 18 butts up against the inside surface 36 of the body wall 34, it seals the entrance site such that fluids and gases do not pass between the flange 18 and the body wall 34 of the entrance site.

After securing the port body 12 to the body wall 34, irrigation of the entry site may be performed, if necessary. Surgical instruments (e.g., endoscopic imaging probes, cutting blades, clamps/suturing devices, laparoscopic instruments, etc.) may then be inserted (and manipulated) into the body cavity through the passageway 30 provided by the port body 12. During use, the orientation of the port body 12 may be manipulated such that it is angled with respect to the orientation of the narrow opening in the body wall at the entrance site. During such use, the body wall exerts forces upon the port body 12. Preferably, the tubular structure 16 is made of rigid material (for example, stainless steel, rigid plastic such as liquid crystal polymer or polycarbonate, glass-filled polycarbonate, or the like) such that the port body 12 does not substantially deform in response to such forces, thereby enabling the tubular structure of passageway 30 to substantially remain unchanged. In this manner, the orientation of the port body 12 may be angled via manipulation of the port body 12 without interfering with insertion, removal or other user manipulation of a medical instrument passing the passageway 30. This enables the medical instrument to freely move through the port body 12 while the orientation of the port body 12 is angled via manipulation of the port body 12. In addition, the flange 18 and retention mechanism 20 are preferably made of flexible material (such as silicon rubber, or synthetic rubber or the like) that enable the flange 18 and retention member 20 to conform to the body wall as the orientation of the port body 12 is angled. This features reduces the forces required to angle the orientation of the port body 12 while providing an effective clamping action and an improved seal between the surfaces of body wall and the flange 18 and retention member 20, respectively.

Figure 4D:
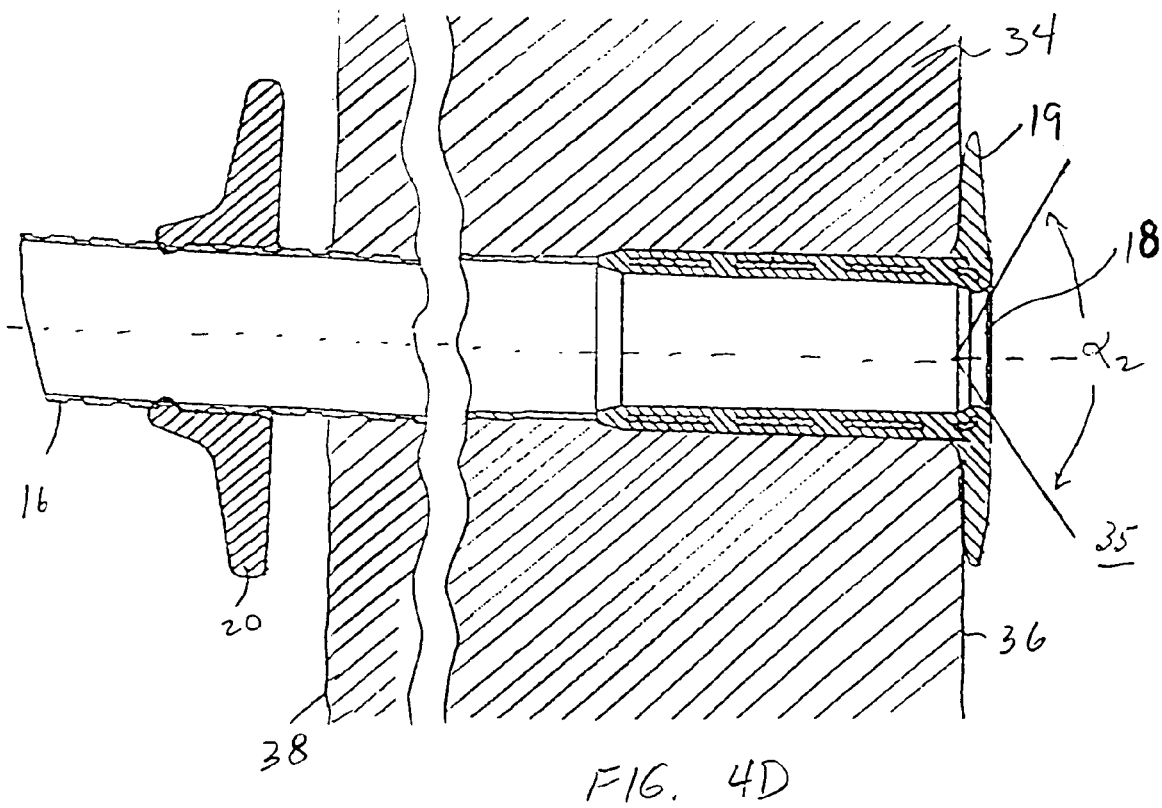
FIGS. 4D and 4E are broken cross-sectional views of the port body of FIGS. 1 and 2 whereby the tubular section is retracted in a proximal direction to provide an improved field of view for the imaging device in accordance with the present invention.
Figure 4E:
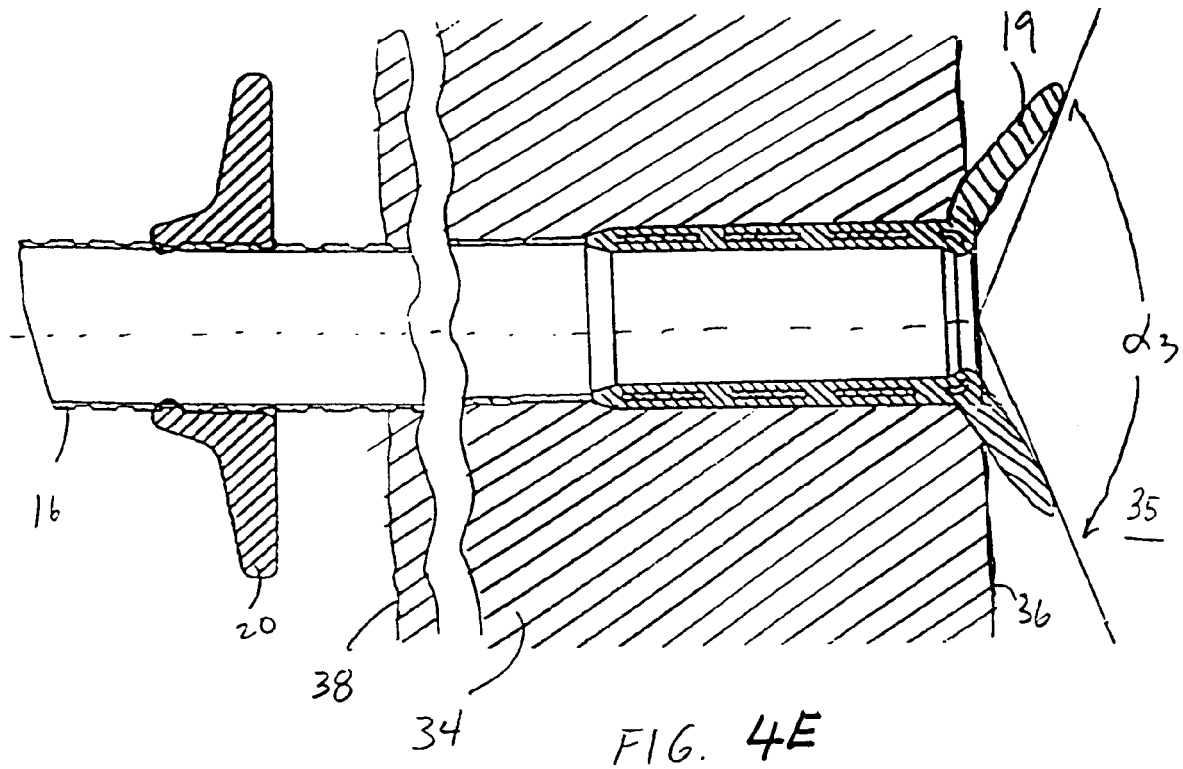

When the surgical port is secured to the body wall 34, the tubular section 16 can be retracted (i.e., pulled in the proximal direction) such that the flange 18 flattens and becomes flush against the inside surface 36 of the body wall 34 in the vicinity of the entrance site as shown in FIG. 4D. Continued retraction of the tubular section 16 causes partial eversion of the flange 18 as it is retracted partially into the body wall 34 as shown in FIG. 4E. Such operations enable an improved field of view for optics of a medical imaging instrument which may be positioned at the juncture of the body wall 34 and a cavity 35; i.e., parallel with the inside surface 36 of the body wall. The widening of the optical field of view that is provided by retraction of the tubular section 16 (which results in the flattening/eversion of the flange 18) is illustrated by the angles $\alpha_1$, $\alpha_2$, $\alpha_3$ in FIGS. 4C-4E, respectively. Note that the maximal field of view $\alpha_1$ of the optics in the configuration of FIG. 4C widens to a maximal field of view $\alpha_2$ (where $\alpha_2 > \alpha_1$) by retraction of the tubular section 16 (which results in the flattening of the flange 18) together with maintaining the position of the optics in line with the inside surface 36 of the body wall 34 as shown in FIG. 4D. The maximal field of view of the optics widens further to a maximal field of view $\alpha_3$ (where $\alpha_3 > \alpha_2 > \alpha_1$) by retraction of the tubular section 16 (which results in the partial eversion of the flange 18) together with maintaining the position of the optics at the same location as shown in FIG. 4E.

The port body 12 is removed from the body wall 34 by pulling the tubular section 16 in the proximal direction, thereby causing eversion of the flange 18. In other words, the resistive forces exerted by the elastic nature of the body wall causes the outer surface 19 of the flexible flange 18 to fold in the distal direction (i.e., in a direction into the body cavity and away from the distal end of the tubular section 16) and radially inward (i.e., toward the longitudinal axis 32 of the tubular section 16) in a manner similar to the partially-everted configuration of FIG. 4C. Once outside the body cavity, the outer surface 19 of the flange 18 deploys back to its original frusto-conical as shown in FIG. 3. In this manner, the flexible flange 18 deforms to provide a decreased cross-sectional diameter as it passes through the narrow opening in the body wall at the entrance site, and returns to an increased cross-sectional diameter when it passes through the body wall and exits the body cavity.

Figure 5:
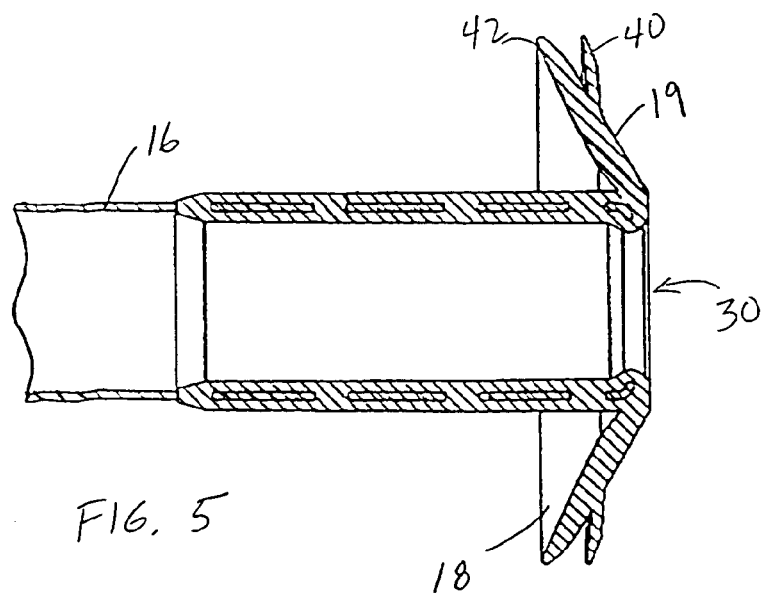
FIG. 5 is a broken cross-section view illustrating an alternate embodiment of the flexible flange in accordance with the present invention.

As shown in FIG. 5, the frusto-conical flange 18 as described above may be modified to include an annular projection 40 that is disposed distal to the proximal edge 42 of the frusto-conical flange 18 and that projects radially outward from the outer surface 19 of the flange 18. In this manner, the annular projection 40 acts like a drip edge that directs fluids around its periphery and thus prevents fluids from flowing over the projection 40 to the passageway 30. This minimizes smearing of optics disposed in the vicinity of the entrance site as described above with respect to FIGS. 4A-4F.

Figure 6A:
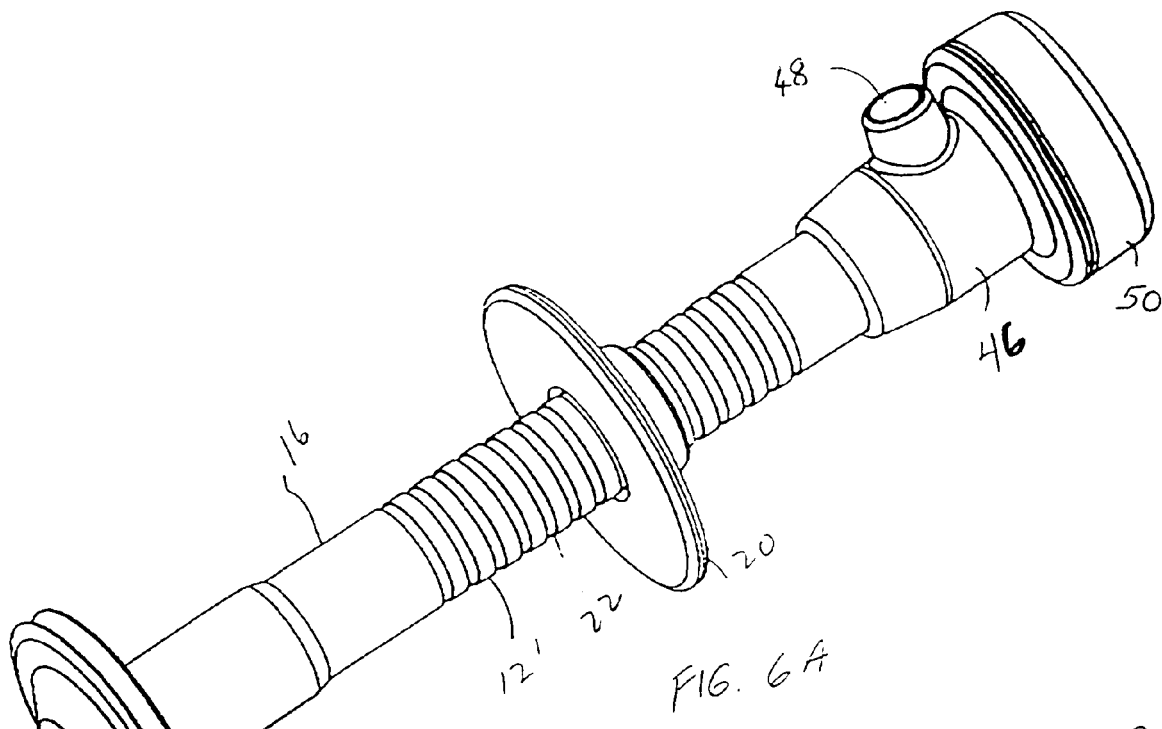
Figure 6B:
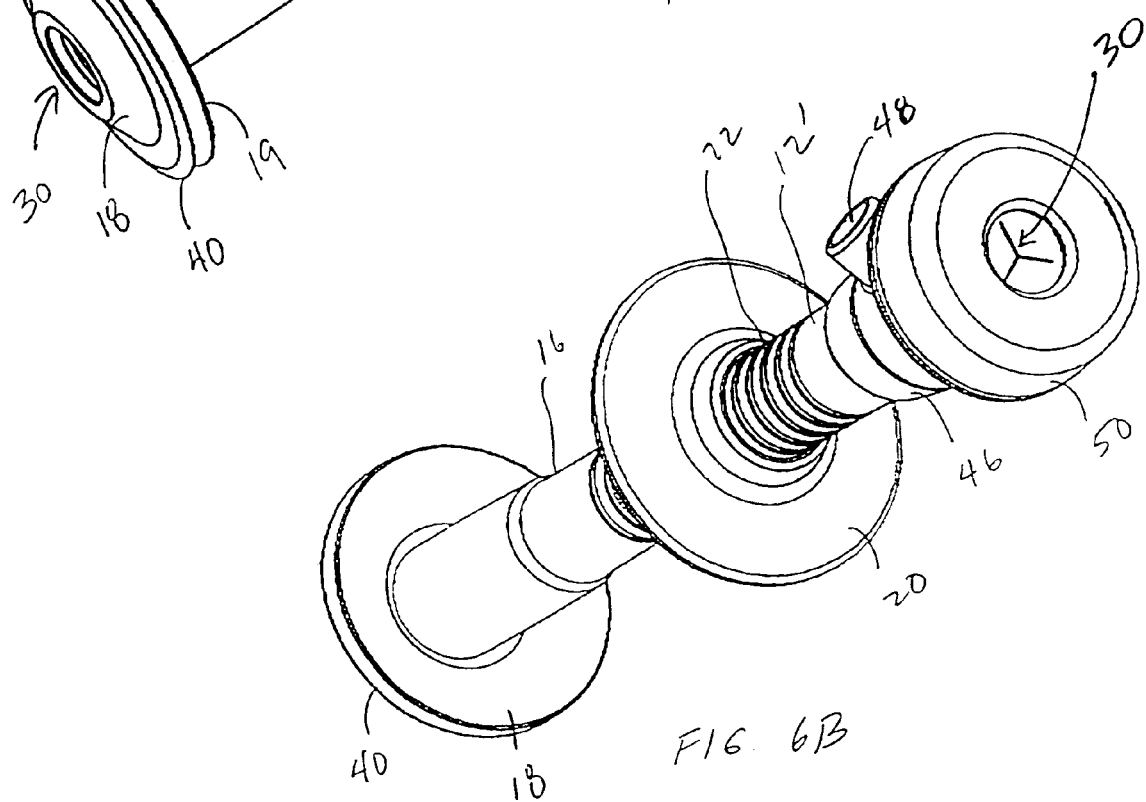

Turning now to FIGS. 6A-6C, there is shown an alternate embodiment of a surgical port device in accordance with the present invention. The port body 12' includes a frusto-conical flange 18 as described above with respect to FIG. 5. In addition, the port body 12' includes a side port section 46 disposed at the proximal end of the tubular section 16. The side port section 46 includes a side port 48 that is in fluid communication with the passageway 30 through the tubular section 16. The side port 48 is used for insufflation via an external pressure source operably coupled to the body cavity through the side port 48. In addition, the port body 12' includes a known valve assembly 50 disposed at the proximal end of the port body 12' that maintains the elevated internal pressures in the body cavity during insufflation while inserting/removing endoscopic instruments through the passageway 30 of the port body 12'. The side port 48 may also be used for flushing as well. It should be appreciated that the side port section 46 (and associated side port 48) may be omitted from the port body 12' while maintaining the valve assembly 50.

There have been described and illustrated herein several embodiments of a surgical port device and methods of operation of the surgical port device. Advantageously, the surgical port devices provide an adjustable distance between the flexible distal flange and a proximal retention member to provide effective clamping action of body tissue therebetween over a wide range of body wall thicknesses, and thus are effective in securely affixing the surgical port to the entrance site over a wide range of body wall thickness. In addition, the surgical port devices of the present invention are simple to use and cost less to manufacture than prior art devices. While particular embodiments of the invention have been described, it is not intended that the invention be limited thereto, as it is intended that the invention be as broad in scope as the art will allow and that the specification be read likewise. Therefore, while the elements of the system have been particularly described with respect to their use with particular medical instruments, it may be used with other types of medical instruments. In addition, the surgical port devices described herein can be designed and manufactured with different sizes (e.g., varying length and cross-sectional diameter of the components), with different diameters, with varying flexibility of the frusto-conical flange and/or varying flexibility of the slidable retention member. In addition, gasket/seals may be integrated at (or near) the distal end of tubular section of the port body in order to maintain the elevated internal pressures in the body cavity during insufflation while inserting/removing medical instruments through the passageway of the port body. It will therefore be appreciated by those skilled in the art that yet other modifications could be made to the provided invention without deviating from its spirit and scope as claimed.

What is claimed is:

1. A surgical port device for insertion through a body wall, comprising:
    a port body including a tubular section having a proximal end opposite a distal end and defining a passageway though which a surgical instrument can be inserted, an exterior surface that extends between said proximal end and said distal end, and a flexible flange disposed at said distal end;
    a retention member that is slidably mated along and surrounding said tubular section such that a distance between said retention member and said flexible flange can be adjusted, whereby said retention member and said flexible flange cooperate to clamp portions of the body wall disposed therebetween and thus effectively clamp said port body in place;
    wherein said flexible flange has a frusto-conical shape with a proximally-concave inner surface adapted to engage the body wall opposite a proximally-concave distal outer surface, said flexible flange extending radially outward from the exterior surface of said tubular section in a proximal direction toward the proximal end of said tubular section, and said flexible flange being adapted to fold radially inward such that said inner surface of said flexible flange contacts the exterior surface of said tubular section during insertion of said port body through a narrow opening in the body wall to thereby reduce diameter of the flexible flange during such insertion, and said flange having an annular lip radially spaced from said tubular section that projects outward from a central portion of said distal outer surface to provide a drip edge adapted to direct fluids around its periphery.

2. A surgical port device according to claim 1, wherein:
said flexible flange is adapted to evert whereby it extends radially outward in a distal direction away from the distal end of said tubular section during removal of said port body through the narrow opening.

3. A surgical port device according to claim 1, wherein:
said tubular section is made of rigid material.

4. A surgical port device according to claim 1, wherein:
said tubular section is adapted to maintain structural integrity in response to forces exerted by said body wall when said tubular section is angled within a narrow opening within the body wall.

5. A surgical port device according to claim 1, wherein:
said retention member is made of flexible material.

6. A surgical port device according to claim 1, wherein:
said retention member is adapted to conform to an outer surface of said body wall when said tubular section is angled within a narrow opening within the body wall.

7. A surgical port device according to claim 1, wherein:
said tubular section has an outer surface having a plurality of annular grooves; and
said retention member includes a pall that slides easily in a distal direction over said plurality of annular grooves and that resists sliding in a proximal direction by engaging one of said plurality of annular grooves.

8. A surgical port device according to claim 1, wherein:
a distal portion of said tubular section includes material surrounding at least one window defined therein, and said flexible flange is integrally formed with said distal portion of tubular section via injection molding of the material through said at least one window.

9. A surgical port device according to claim 8, wherein:
said distal end of said tubular section is turned inward.

10. A surgical port device according to claim 1, wherein:
said flexible flange comprises a hydrophobic material.

11. A surgical port device according to claim 1, wherein:
said tubular section and said flexible flange define a passageway therethrough.

12. A surgical port device according to claim 11, further comprising:
an obturator including a rod-like section having a handle at its proximal end and a conically-tapered tip at its distal end, wherein said rod-like section and tip are sized to be inserted into said passageway such that said tip extends from the distal end of said flexible flange.

13. A surgical port device according to claim 11, further comprising:
a side port, in fluid communication with said passageway.

14. A surgical port device according to claim 11, further comprising:
a valve assembly at a proximal end of said tubular section.

15. A surgical port device according to claim 1, wherein:
said annular lip projects radially outward from said central portion of said distal outer surface.

* * * * *